(12) United States Patent
Birnbaum et al.

(10) Patent No.: US 7,018,339 B2
(45) Date of Patent: Mar. 28, 2006

(54) METHOD FOR PROCESSING HEART RATE INFORMATION IN A PORTABLE COMPUTER

(75) Inventors: Burton H. Birnbaum, Woodmere, NY (US); Ron McPhee, Albuquerque, NM (US); Jeff Collins, Albuquerque, NM (US); Robert Montenegro, Albuquerque, NM (US); Paul Gibson, Albuquerque, NM (US)

(73) Assignee: Polar Electro Oy, Kempele (FI)

( * ) Notice: Subject to any disclaimer, the term of this patent is extended or adjusted under 35 U.S.C. 154(b) by 392 days.

(21) Appl. No.: 10/083,723

(22) Filed: Feb. 25, 2002

(65) Prior Publication Data

US 2003/0167079 A1    Sep. 4, 2003

(51) Int. Cl.
*A61B 5/024*    (2006.01)
(52) U.S. Cl. .................... 600/508; 128/903
(58) Field of Classification Search ........ 600/508–509, 600/510–523; 128/903; 607/30–32, 59, 607/60
See application file for complete search history.

(56) References Cited

U.S. PATENT DOCUMENTS

| | | | |
|---|---|---|---|
| 5,113,869 A * | 5/1992 | Nappholz et al. ........... 600/508 |
| 5,417,222 A * | 5/1995 | Dempsey et al. ........... 600/509 |
| 5,598,849 A | 2/1997 | Browne | |
| 5,690,119 A | 11/1997 | Rytky et al. | |
| 5,921,890 A | 7/1999 | Miley | |
| 5,921,891 A | 7/1999 | Browne | |
| 6,002,982 A | 12/1999 | Fry | |
| 6,015,093 A | 1/2000 | Barrett et al. | |
| 6,042,009 A | 3/2000 | Barrett et al. | |
| 6,139,494 A | 10/2000 | Cairnes | |
| 6,148,262 A | 11/2000 | Fry | |
| 6,308,099 B1 * | 10/2001 | Fox et al. ..................... 607/31 |

OTHER PUBLICATIONS

"Polar S810 Heart Rate Monitor User's Manual", Apr. 23, 2001.

* cited by examiner

*Primary Examiner*—Robert E. Pezzuto
*Assistant Examiner*—Kristen Mullen
(74) *Attorney, Agent, or Firm*—Hoffmann & Baron, LLP (57) ABSTRACT

An apparatus and method for processing heart rate information by wirelessly transferring the information between a heart rate monitor and a personal computer device (PCD). The information includes programming information and heart rate or training information collected during use of the heart rate monitor. The PCD may include a personal digital assistant (PDA), a pocket personal computer (pocket PC), or a laptop computer. The information is transferred over an infrared, sonic, audible, ultrasonic, magnetic, radio frequency, IEEE 802.11, or Bluetooth-based communication link.

22 Claims, 10 Drawing Sheets

METHOD FOR PROCESSING HEART RATE INFORMATION IN A PORTABLE COMPUTER

COPYRIGHT NOTICE

A portion of the disclosure of this document contains material that is subject to copyright protection. The copyright owner has no objection to the facsimile reproduction of the patent disclosure, as it appears in the U.S. Patent and Trademark Office patent files or records, but otherwise reserves all copyright rights whatsoever.

BACKGROUND OF THE INVENTION

1. Field of the Invention

The present invention relates generally to heart rate monitors and more particularly to the processing of heart rate information in a portable computer device including monitoring by a heart rate monitor and wirelessly transferring the heart rate information between the heart rate monitor and the portable computer device.

2. Description of the Related Art

A person's heart rate during exercise is measured with a heart rate monitor (HRM) in terms of the number of heartbeats that occur during a unit of time e.g., beats per minute. The HRM typically includes a chest unit that detects an electrical signal generated by the heart and displays the measured heart rate on a display unit. The display unit can additionally display indicators, such as predetermined heart rate limits or target zones.

Conventional HRMs advantageously provide the user with vast flexibility in terms of programmability of features. Quite often this advantage evolves into a detriment, particularly with users that do not have the ability, time, or interest to become familiar with a multitude of features and the procedures required to program them.

Thus, it would be advantageous if these features were somehow made more user-friendly by making them accessible in a format more readily understandable by the general public. Such accessibility should, if possible, include the ability to both read and write programming and measurement information. However, since HRMs are typically designed to be rugged, portable, and lightweight, the manufacturer is severely limited in the amount of hardware and software that can be added to accommodate additional user-friendly features that would significantly improve interoperability with the user.

The popularity and familiarity of the general public with portable, handheld, or pocket portable computer devices (referenced herein as "PCDs") and other related devices has and continues to grow. However, conventional methods of transferring information to and from HRMs have been limited to communication via telemetric or magnetic means, which are not typically supported by PCDs.

One protocol supported by a growing number of these devices is referred to as "Bluetooth", which is the name given to a new technology standard using short-range radio links. Bluetooth is intended as a replacement for cables connecting portable and/or fixed electronic devices. The standard defines a uniform structure that enables a wide range of devices to communicate with each other while requiring only minimal user interaction.

Figure 1:
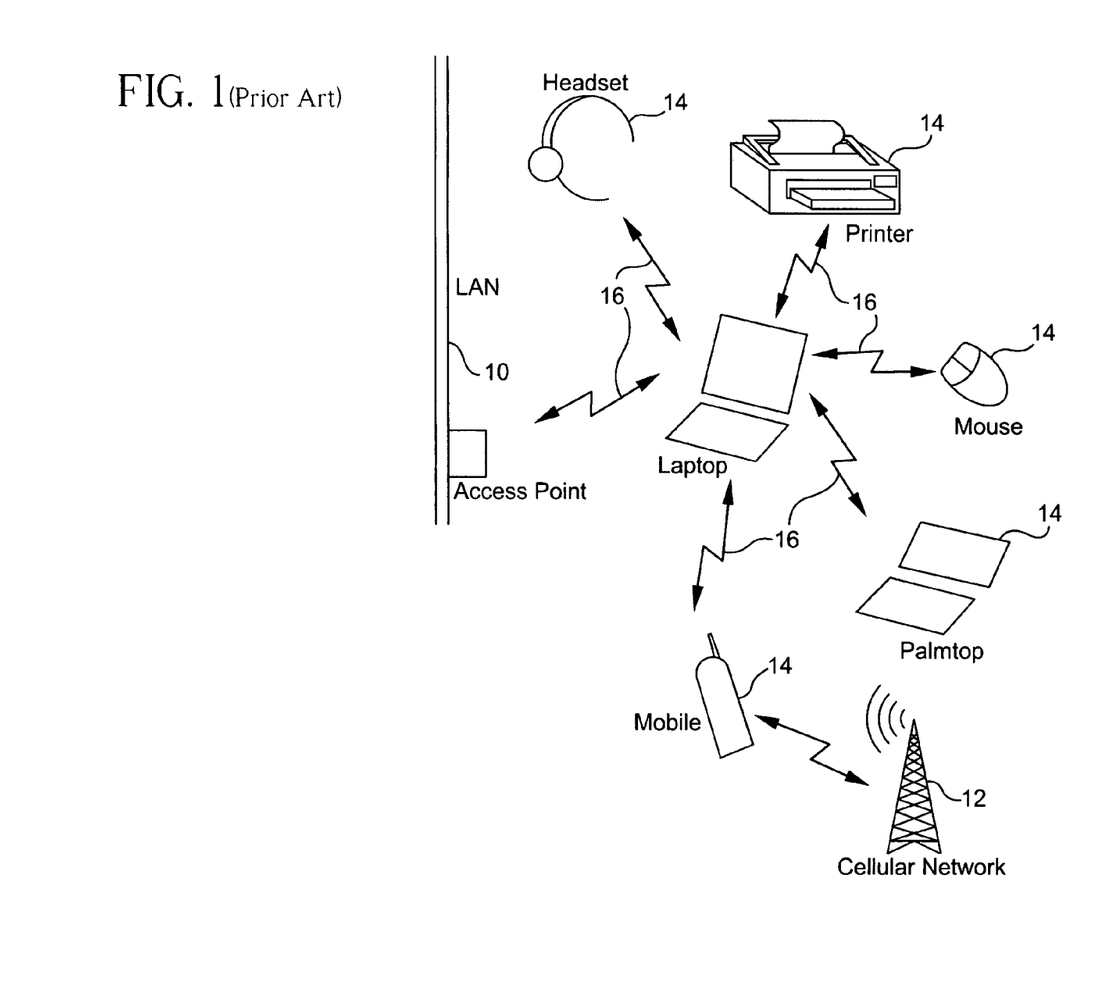
FIG. 1 is a block diagram of a system having wireless connectivity implemented by the conventional Bluetooth protocol.

Its key features are robustness, low complexity, low power, and low cost. As shown in FIG. 1, the technology also offers wireless access to local area networks (LANs) 10, mobile phone networks 12, and the Internet for a host of home appliances and portable interfaces 14.

The standard is aimed at achieving global acceptance so that any Bluetooth device, anywhere in the world, can connect to other Bluetooth devices in its proximity, regardless of the manufacturer. Bluetooth-enabled electronic devices connect and communicate wirelessly via short-range, ad hoc networks called piconets 16.

Each unit can simultaneously communicate with up to seven other units per piconet. Moreover, each unit can simultaneously belong to several piconets 16. These piconets 16 are established dynamically and automatically as Bluetooth devices enter and leave the radio proximity.

The motivation for Bluetooth comes from both a technology push and a market pull. The ability to pack more transistors on smaller areas of silicon has made embedded devices capable of running complex protocols. Embedded controllers in devices are now capable of being programmed, controlled, and used in various intelligent ways. Thus, such devices can now be embedded into the user's work and home areas.

Techniques are available to connect these embedded devices to the Internet, thus forming a so-called "embedded Internet". Significant progress has been made in developing small and inexpensive sensors that can receive useful signals from the user environment without user interaction or explicit commands. New types of electronic tags, which may be incorporated in Bluetooth units, have become available that may be used to specify the type of information exchanged. These tags enable interaction between a variety of devices.

This has also opened the possibility for creating an "ubiquitous computing" environment. In this environment, the devices are controlled and activated by a combination of intelligent systems and strategically located sensors that work without explicit user support. The facility to automate depends heavily on the ability of devices to communicate wirelessly with each other, intelligent central servers, information repositories, sensors, and actuators. Bluetooth provides a solution to these requirements.

The immediate need for Bluetooth came from the desire to connect peripherals and devices without cables. Bluetooth was further fueled by the demand for mobile and wireless access to LANs, Internet access over mobile phones, and other existing networks in which the backbone is wired but the interface is free to move. This not only makes the network easier to use but also extends its reach. The advantages and rapid proliferation of LANs suggest that setting up personal area networks, that is, connections among devices in the proximity of the user will have many beneficial uses.

Bluetooth may also be used in home networking applications. With increasing numbers of homes having multiple PCDs, the need for networks that are simple to install and maintain is growing. There is also a commercial need to provide "information push" capabilities, which is important for handheld PCDs and other mobile devices.

The primary strength of Bluetooth is its ability to simultaneously handle both data and voice transmissions, allowing such innovative solutions as a mobile hands-free headset for voice calls and print-to-fax capability. These uses suggest that a technology like Bluetooth is extremely useful and will have a significant effect on the way information is accessed and used.

Although, originally conceived to enable the design of universal wireless connections for laptops, PCDs, and cellular telephones, it is apparent that there are many other applications for the Bluetooth standard. Thus, Bluetooth not only tries to overcome the limitations of wired networks, but also offers a variety of other services and creates opportunities for new usage models.

Therefore, it would be advantageous to provide a method and apparatus to bidirectionally transfer setting information, which may be used to program a heart rate monitor, and transfer measured data, such as heart rate and training information, between a heart rate monitor and a PCD. Further, it would be advantageous to simplify the process of programming the heart rate monitor and reduce the amount of time required by the user to initialize the monitor prior to its use. In addition, it would be advantageous to enable measured heart rate and training information to be downloaded, processed, and analyzed by the PCD.

It is an object of the present invention to provide an effective and reliable method and apparatus for processing heart rate information by wirelessly exchanging the information between a heart rate monitor and a PCD.

It is a further object of the present invention to provide a method and apparatus for bidirectionally exchanging setting information, which may be used to program a heart rate monitor, between the heart rate monitor and a PCD.

It is still a further object of the present invention to provide a method and apparatus for processing measured data, such as heart rate and training information, by exchanging the information between a heart rate monitor and a PCD.

It is another object of the present invention to provide a method and apparatus for processing information in a heart rate monitor and a PCD by exchanging the information via infrared, sonic, ultrasonic, radio frequency, magnetic, IEEE 802.11, and/or Bluetooth-based communication links.

It is still another object of the present invention to provide a method and apparatus for processing information in a heart rate monitor and a PCD, which substantially simplify the process of programming the monitor and reduce the amount of time required by the user to initialize the heart rate monitor prior to its use.

It is yet another object of the present invention to provide a method and apparatus for processing information between a heart rate monitor and a PCD, which enable measured heart rate and training information to be downloaded, processed, and analyzed by the PCD.

SUMMARY OF THE INVENTION

These and other goals and objectives of the present invention provide a method of processing heart rate information by wirelessly exchanging the information between a heart rate monitor and a portable computer device, which includes the steps of initiating a connect mode in the heart rate monitor, initiating transfer software in the portable computer device, and transferring the information between the heart rate monitor and the portable computer device through a communication link.

The connect mode enables an infrared, sonic, audible, ultrasonic, magnetic, radio frequency, and/or Bluetooth-based communication link to be established with the heart rate monitor. The transfer software controls the transfer of information between the heart rate monitor and the portable computer device through the communication link.

The present invention also provides a system for processing and wirelessly exchanging heart rate information, which includes a heart rate monitor and a portable computer device. The heart rate monitor has a connect mode, which enables an infrared, sonic, audible, ultrasonic, magnetic, radio frequency, and/or Bluetooth-based communication link to be established with the heart rate monitor. The portable computer device includes transfer software, which controls the transfer of information between the heart rate monitor and the portable computer device through the communication link.

The present invention further provides a heart rate monitor that wirelessly exchanges information with a portable computer device. The heart rate monitor includes a wireless interface circuit and a connect mode. The connect mode enables an infrared, sonic, audible, ultrasonic, magnetic, radio frequency, Bluetooth-based wireless communication link, and/or other wireless links not previously contemplated to be established with the portable computer device through the wireless interface circuit.

The present invention still further provides a portable computer device that wirelessly exchanges information with a heart rate monitor. The portable computer device includes a wireless interface circuit and transfer software. The transfer software controls the transfer of information between the heart rate monitor and the portable computer device on an infrared, sonic, audible, ultrasonic, magnetic, radio frequency, Bluetooth-based wireless communication link through the wireless interface circuit.

These and other objects, features, and advantages of this invention will become apparent from the following detailed description of illustrative embodiments thereof, which is to be read in connection with the accompanying drawings.

DETAILED DESCRIPTION OF THE PREFERRED EMBODIMENTS

Figure 2A:
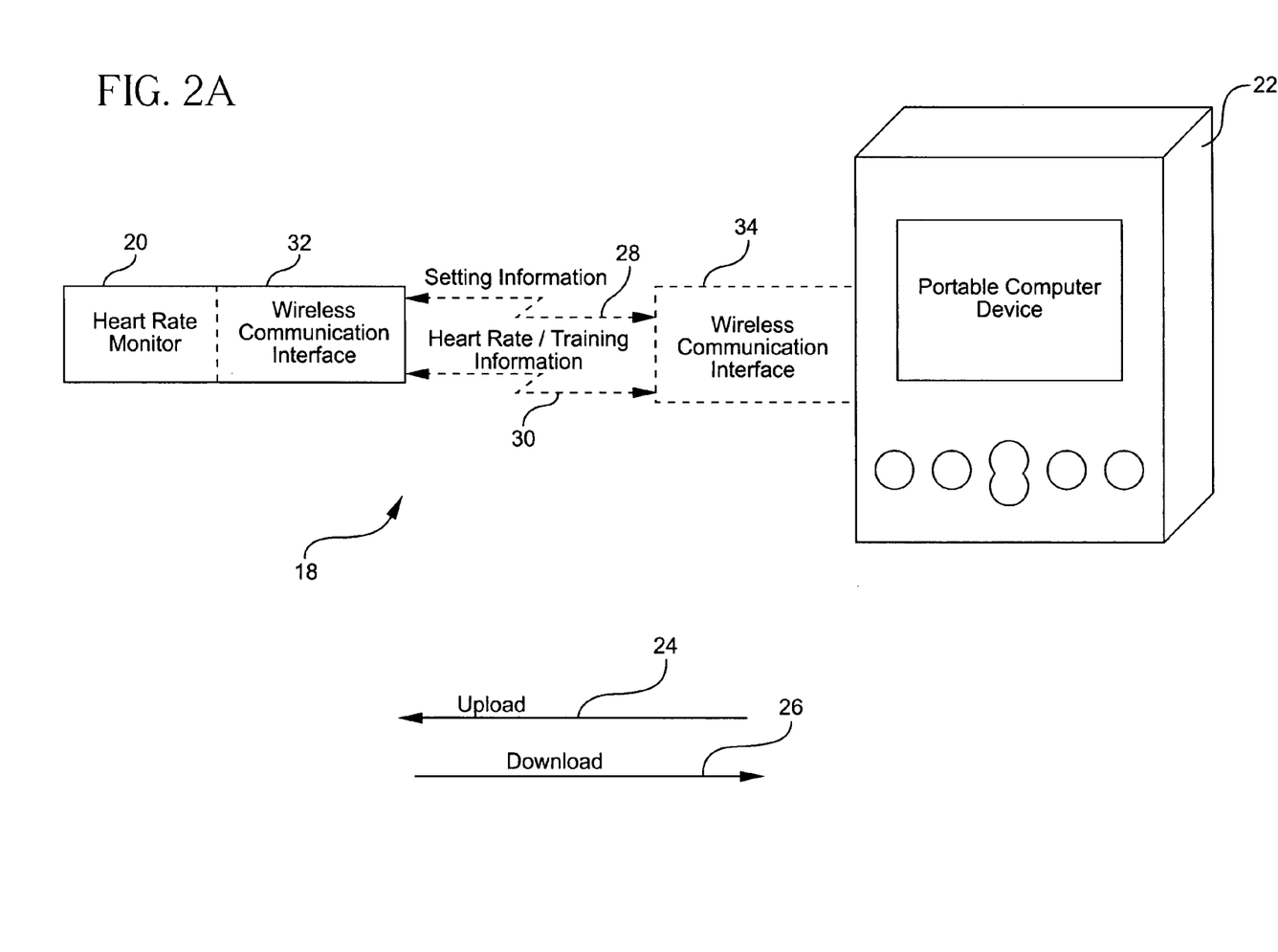
FIG. 2A is a block diagram of a system for wirelessly exchanging information between a heart rate monitor and a portable computer device formed in accordance with the present invention.

FIG. 2A is a block diagram showing the preferred embodiment of a system 18 for processing information by exchanging heart rate information between a heart rate monitor 20 and a portable computer device 22. The portable computer device (PCD) 22 is preferably a personal digital assistant (PDA), but may be or include a pocket personal computer (pocket PC), a laptop computer, or other portable computer devices not previously contemplated.

The direction of information flow is generally shown by arrows 24, 26. Specifically, arrow 24 defines the upload of information to be preferably from the PCD 22 to the heart rate monitor 20. Similarly, arrow 26 defines the download of information to be preferably from the heart rate monitor 20 to the PCD 22.

As shown in FIG. 2A, setting information is preferably transferred bidirectionally to and from the heart rate monitor 20, as shown by a dotted arrow 28. Heart rate and/or training information is preferably downloaded from the heart rate monitor 20 to the PCD 22, as shown by dotted arrow 30. The dotted arrows 28, 30 represent the wireless transfer of information preferably by an infrared communication link, but may also be transferred by a sonic, audible, ultrasonic, magnetic, radio frequency, Bluetooth-based, IEEE 802.11, and/or other wireless links not previously contemplated wireless communication link.

Setting information preferably includes information used to program features, variables, constants, and the like within the heart rate monitor, such as a user identification, user name, or logo for easier receiver recognition in multi-user situations, a heart touch function to show the current heart rate limits, and an options lock function. Heart rate and/or training information refers to the data collected or measured from the user during his use of the heart rate monitor 20.

Wireless communication interfaces 32, 34 preferably enable the heart rate monitor 20 and the PCD 22, respectively, to receive and transmit information wirelessly. These interfaces 32, 34 may be self-contained within the heart rate monitor 20 and PCD 22 or may be added to pre-existing devices as external units.

Figure 2B:
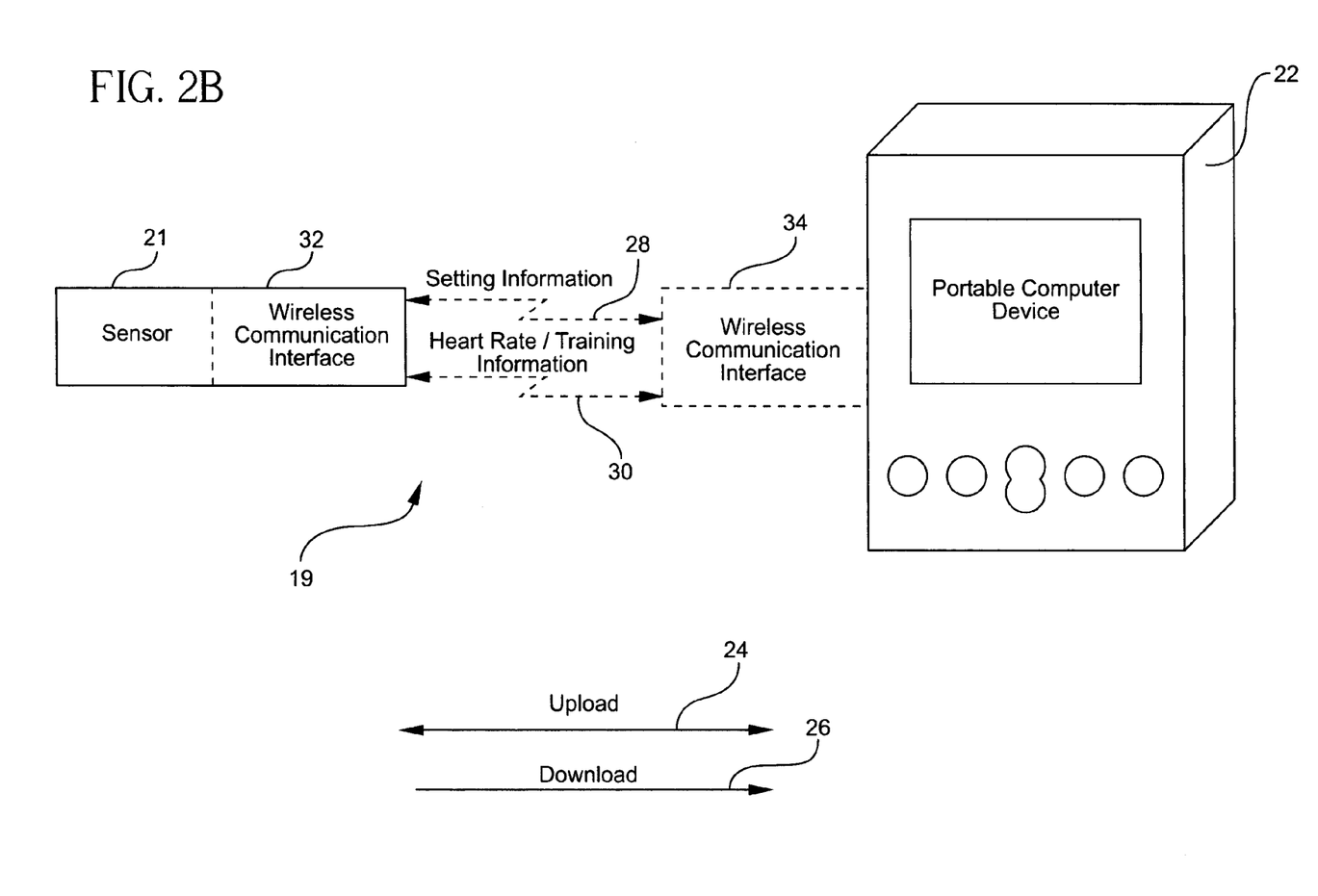
FIG. 2B is a block diagram of a system for wirelessly exchanging information between a heart rate sensor and a portable computer device formed in accordance with the present invention.

FIG. 2B shows an alternative embodiment 19 of the system 18 shown in FIG. 2A in which setting information 28 or heart rate/training information 30 is preferably transferred directly between a heart rate sensor 21 and the PCD 22. This embodiment avoids the need for transferring the information to or from the heart rate monitor 20 prior to transferring it to or from the PCD 22.

Figure 3:
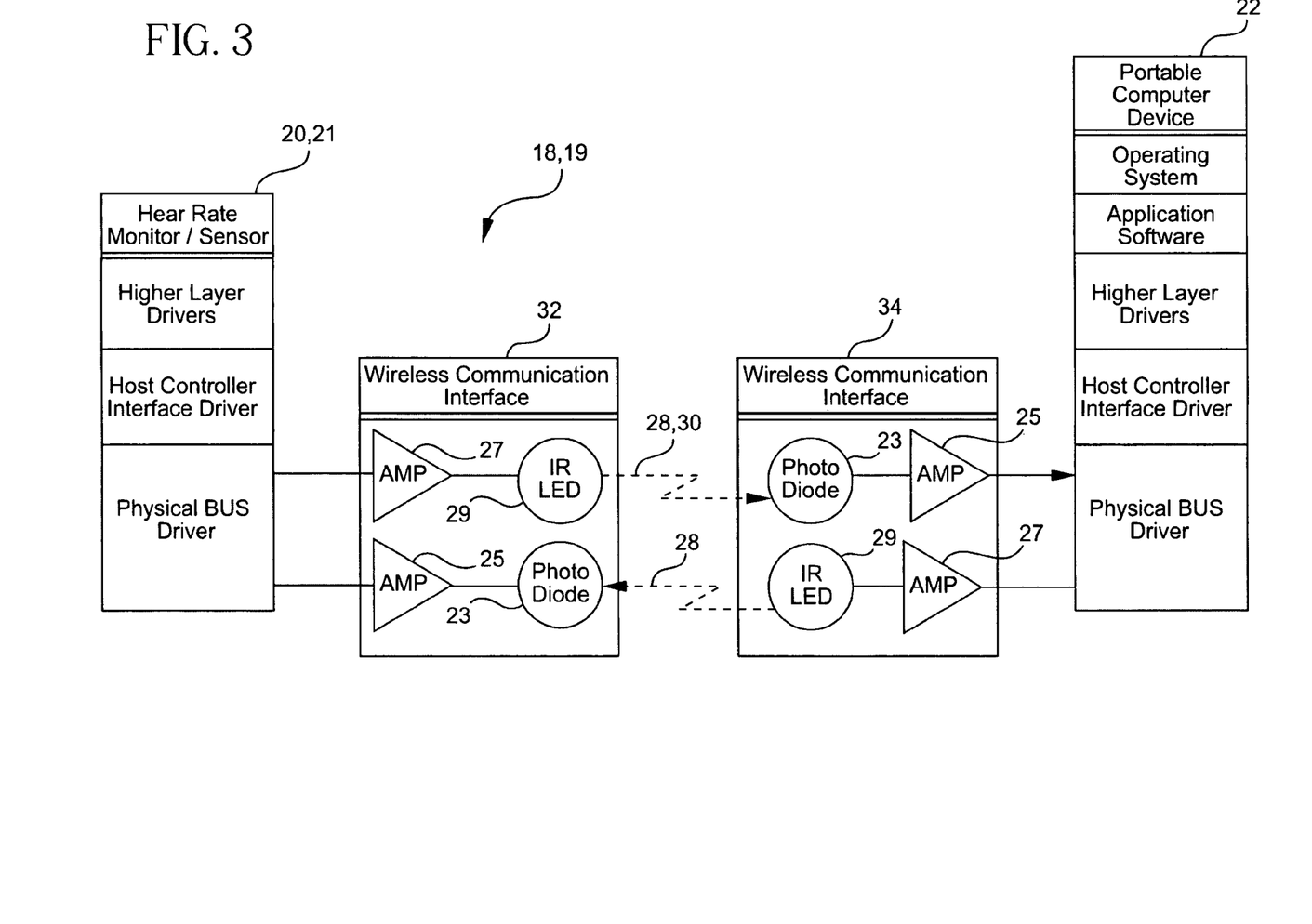
FIG. 3 is a block diagram of an embodiment of the systems shown in FIGS. 2A and 2B utilizing an infrared communication link.

FIG. 3 is a block diagram of an embodiment of the systems 18, 19 shown in FIGS. 2A and 2B utilizing an infrared communication link. Both the heart rate monitor/sensor 20, 21 and the PCD 22 preferably include at least three levels of software, which are a physical bus driver, a host controller interface driver, and higher layer drivers.

The physical bus driver provides low-level software control of a physical bus between the wireless communication interface 32 and the heart rate monitor/sensor 20, 21. The host controller interface receives and transmits data from the physical bus driver in a format appropriate for processing by the higher layer drivers. The software in the PCD 22 interfaces in a similar manner to its respective wireless communication interface 34.

Each of the wireless communication interfaces 32, 34 preferably includes an infrared receive path and an infrared transmit path to accommodate the bidirectional flow of setting information 28 and heart rate/training information 30. The infrared receive path preferably includes a photo-diode 23 followed by an amplifier 25 and the infrared transmit path preferably includes an amplifier 27 followed by an infrared light emitting diode (IR LED) 29.

Setting information 28 is, for instance, transferred by the physical bus driver in the PCD 22 to the amplifier 27 in its respective wireless communication interface 34 preferably as a digital signal. The digital signal is then translated to pulses of infrared light by the IR LED 29, which are transmitted to the wireless communication interface 32 associated with the heart rate monitor/sensor 20, 21. The corresponding photo-diode 23 in the wireless communication interface 32 receives the infrared pulses and preferably translates these pulses into a digital signal, which is then applied to the amplifier 25.

The amplified signal is then input by the heart rate monitor/sensor 20, 21 and applied by the various levels of software in the heart rate monitor/sensor 20, 21 as setting information. The setting information 28 or heart rate/training information 30 is transferred in the opposite direction, that is, from the heart rate monitor/sensor 20, 21 to the PCD, in a similar manner to that described above.

Figure 4:
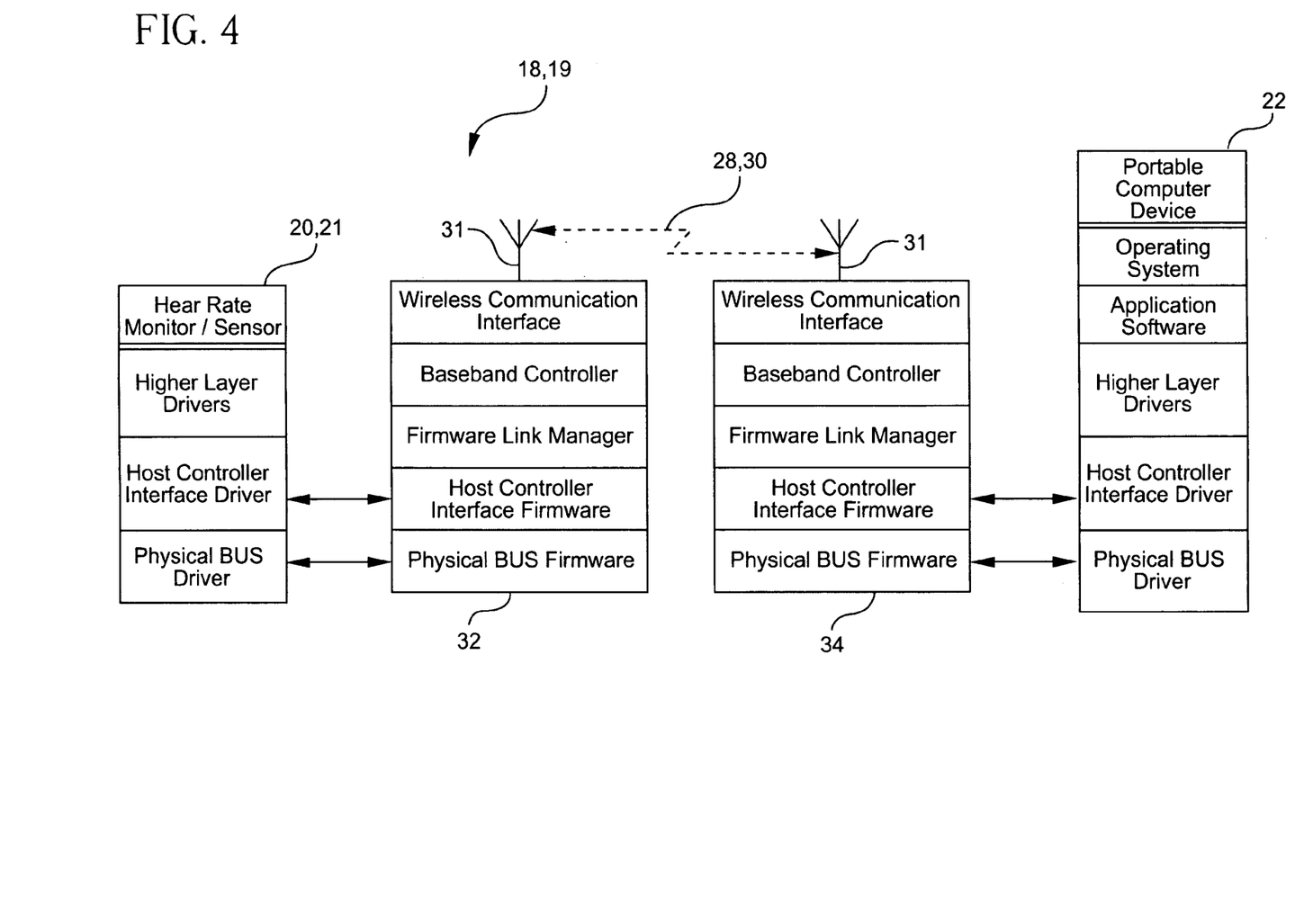
FIG. 4 is a block diagram of an embodiment of the systems shown in FIGS. 2A and 2B utilizing a Bluetooth communication link.

FIG. 4 is a block diagram of an embodiment of the systems 18, 19 shown in FIGS. 2A and 2B utilizing a Bluetooth communication link. As described above with respect to FIG. 3, both the heart rate monitor/sensor 20, 21 and the PCD 22 preferably include a physical bus driver, a host controller interface driver, and higher layer drivers.

Each of the wireless communication interfaces 32, 34 preferably includes at least four levels of software, which are physical bus firmware, host controller interface firmware, link manager firmware, and a baseband controller. Physical bus firmware monitors and controls the physical bus between the heart rate monitor/sensor 20, 21 and the wireless communication interface 32. Host controller interface firmware performs tasks initiated by the host controller interface driver in the heart rate monitor/sensor 20, 21.

Link manager firmware in the wireless communication interface 32 maintains upper level control of the communication link in accordance with Bluetooth specifications. Baseband controllers transmit and receive setting information 28 and heart rate/training information 30 between the wireless communication interfaces 32, 34 over the specified bandwidth via antennas 31 associated with both wireless communication interfaces 32, 34. The PCD 22 and its corresponding wireless communication interface 34 interact in a similar manner to that described above with respect to the heart rate monitor/sensor 20, 21.

Figure 5:
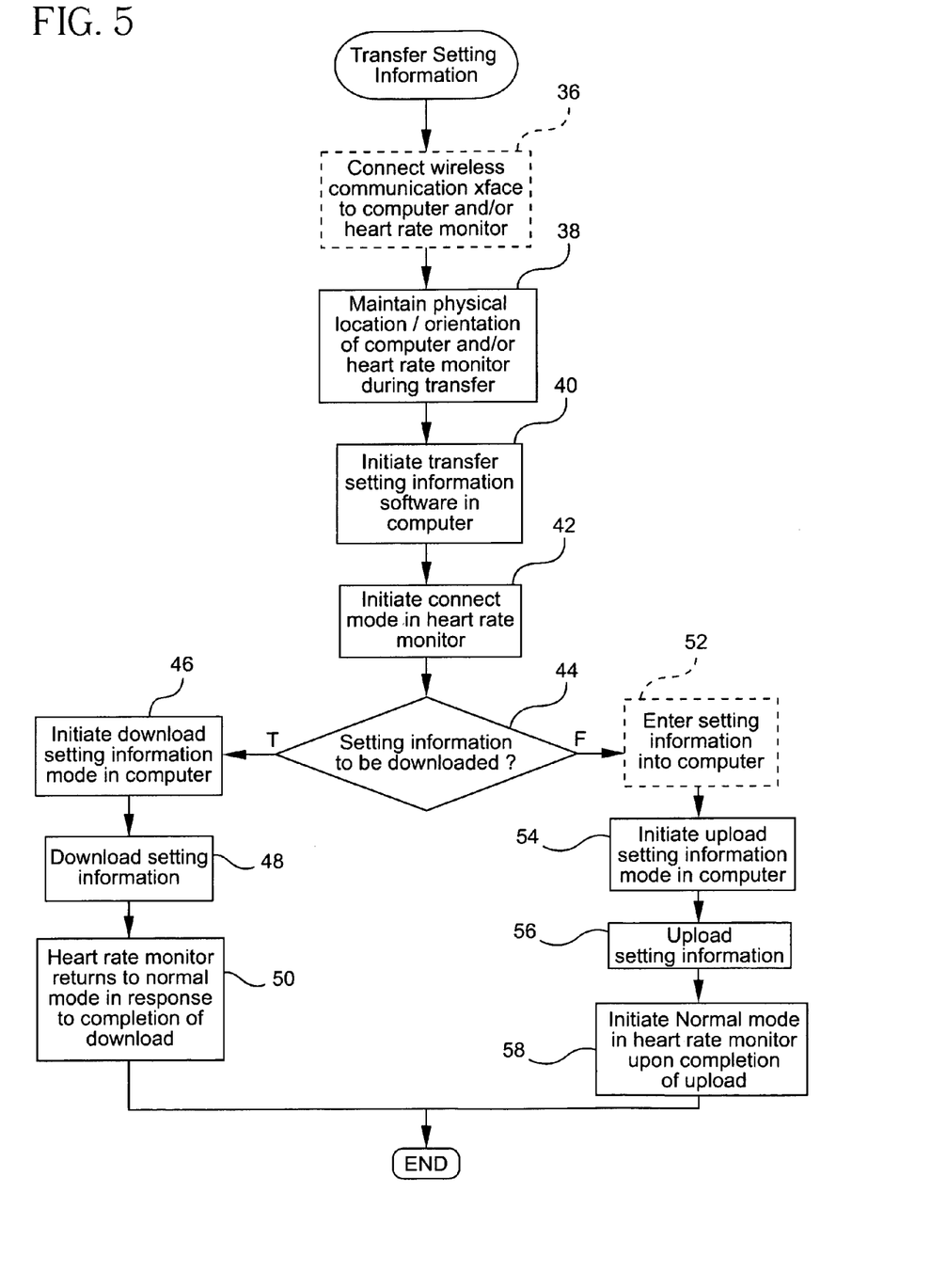
FIG. 5 is a flowchart of a method for wirelessly exchanging setting information between a heart rate monitor and a portable computer device in accordance with the present invention.

FIG. 5 is a flowchart of a preferred method for transferring setting information using the system 18 formed in accordance with the present invention. The wireless communication interface is connected to the PCD and heart rate monitor, if required, in step 36, and the physical location and orientation of the heart rate monitor and PCD are maintained in compliance with wireless requirements during the transfer of information between them in step 38. Transfer setting information software is initiated in the PCD in step 40, and a connect mode is initiated in the heart rate monitor, which prepares the heart rate monitor for the wireless communication link, in step 42.

In step 44, if the setting information is to be downloaded from the heart rate monitor to the PCD, a download setting information mode is initiated in the PCD in step 46. The setting information is then downloaded in step 48, the heart rate monitor returns to a normal mode in response to completion of the download of setting information in step 50, the method ends.

If, in step 44, setting information is to be uploaded, the setting information either resides in the PCD or is entered into the PCD in step 52, and an upload setting information mode is initiated in the PCD in step 54. The setting information is then uploaded from the PCD to the heart rate monitor in step 56. The normal mode is initiated in the heart rate monitor upon completion of the upload of setting information in step 58, following which the method ends.

Figure 6:
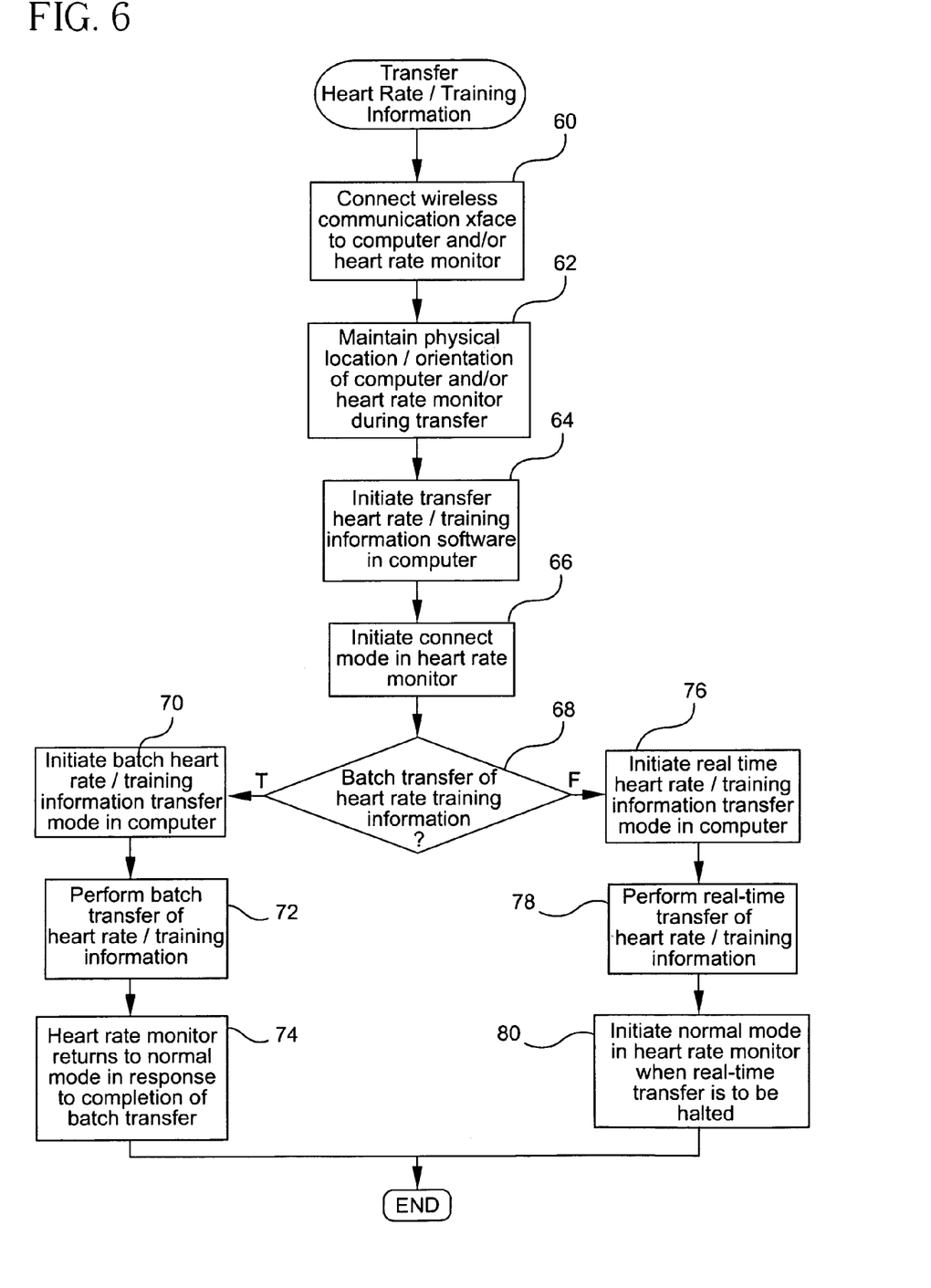
FIG. 6 is a flowchart of a method for wirelessly exchanging heart rate/training information between a heart rate monitor and a portable computer device in accordance with the present invention.

FIG. 6 is a flow chart of a preferred method for transferring heart rate/training information between the heart rate monitor and the PCD shown in FIG. 2A. If required, the wireless communication interfaces are connected to the PCD and/or heart rate monitor in step 60. The physical location and orientation of the heart rate monitor and the PCD are maintained in compliance with wireless requirements during the transfer of heart rate/training information in step 62.

Transfer heart rate/training information software is initiated in the PCD in step 64, and the connection mode is initiated in the heart rate monitor in step 66. If, in step 68, a batch transfer of heart rate/training information is to be performed, a batch heart rate/training information transfer mode is initiated in the PCD in step 70. The batch transfer of heart rate/training information is performed in step 72, the heart rate monitor returns to the normal mode in response to completion of the batch transfer of heart rate/training information in step 74, and the method ends.

If, in step 68, a batch transfer of heart rate/training information is not to be performed, a real-time heart rate/training information transfer mode is initiated in the PCD in step 76, and the real-time transfer is performed in step 78. The normal mode is then initiated in step 80 when the real-time transfer heart rate/training information is to be halted, after which the method ends.

Figure 7:
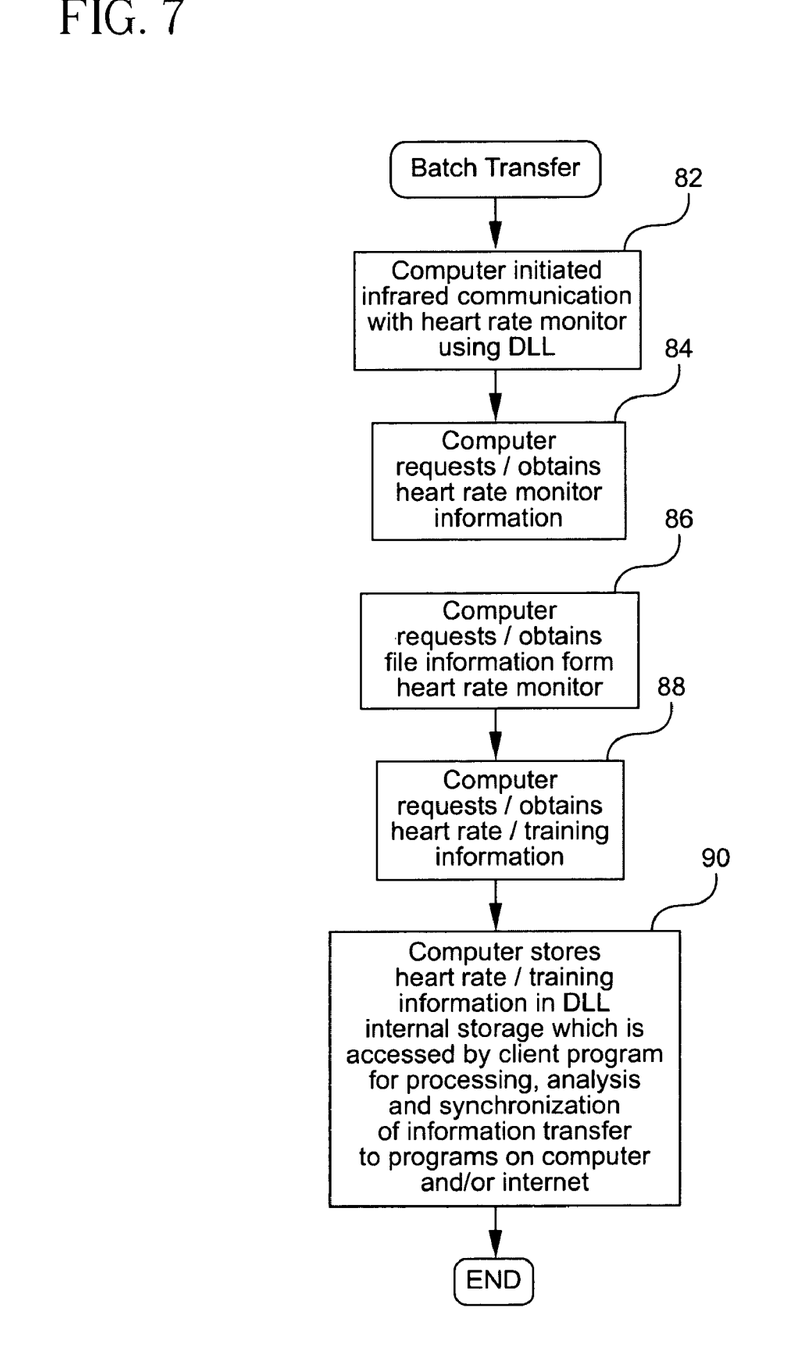
FIG. 7 is a flowchart of a method for wirelessly exchanging batch heart rate/training information between a heart rate monitor and a portable computer device in accordance with the present invention.

FIG. 7 shows a flow chart that provides greater detail concerning step 72 shown in FIG. 6. In step 82, the PCD preferably initiates infrared communication with the heart rate monitor using a dynamic link library (DLL), and the PCD requests information regarding the heart rate monitor using the DLL in step 84. In step 86, the PCD requests and obtains file information from the heart rate monitor, and then requests and obtains specific heart rate information from the heart rate monitor in step 88.

The heart rate information is stored in the internal storage of the DLL in the PCD in step 90, which enables a client program, which is also preferably in the PCD, to access this information. The heart rate/training information may be further processed, analyzed, and/or synchronized with information transfers to programs on the PCD and/or Internet.

The following discussion provides instructions, which include source C-code, for a preferred method of obtaining an infrared connection between S610, S710, S810, and E600 heart rate monitors and a PCD preferably using a DLL software platform HRMCom.DLL. A header file HRMCom.h for the DLL software platform HRMCom.DLL is incorporated as a portion of this document as an appendix and is incorporated herein by reference. The header file HRMCom.h includes additional information regarding calls and parameters. Both the heart rate monitors listed above and the DLL software platform are commercially available from Polar Electro Oy, Professorintie 5, FIN-90440, Kempele, Finland.

The following instructions and source code are referenced to the steps shown in the flowchart of FIG. 7. Comments to the source code are preceded by double backslashes. Accordingly, in step 82, an infrared connection is initiated by calling the following function:

```
if (!fnHRMCom_ResetIRCommunication (0));                    (1)
{
    // Resetting IR connection was not successful
    break;                                                   (2)
}
```

A serial port on the heart rate monitor is opened and a communication thread is started by using the following function call:

```
if(!fnHRMCom_StartIRCommunication (0, "COM1:"));            (3)
{
    // Port couldn't be opened, stop connection thread
    fnHRMCom_EndIRCommunication (FALSE);                     (4)
    break;                                                   (5)
}
```

A colon is preferably used at the end of a port name, such as communication ports 1–9. If an internal infrared port is used, then HRMCOM_PARAM_INTERNALIR is preferably used as a first parameter. If the function call directly above returns TRUE, the infrared connection to the heart rate monitor has been successfully established.

In step 84, the PCD is able to request and obtain heart rate monitor information by using the following source code:

```
    POLAR_SSET_GENERAL psg;                                  (6)

POLAR_SSET_MONITORINFO psmi; (7)
//Fill general information
    ZeroMemory (&psg, sizeof(psg));                          (8)

psg.iSize=sizeof (psg); (9)

psg.iconnection=HRMCOM_CONNECTION_IR;                    (10)

psg.bConnectionDlg=TRUE;                                 (11)

psg.hOwnerWnd=hDlg;                                      (12)
//Owner window handle
//Reset monitor information
    ZeroMemory (&psmi, sizeof(psmi));                        (13)
//Read monitor info from HR monitor using IR
```

```
if (!fnHRMCom_ReadMonitorinfo (&psg, &psmi));               (14)
{
    // Reading failed
}
```

By calling the function fnHRMCom_ReadMonitorInfo with the parameters indicated above, a dialog of the connection is preferably displayed on the PCD. If the function call directly above returns TRUE, the structure psmi preferably includes the requested information concerning the heart rate monitor.

In step 86 of FIG. 7, information concerning the files containing the heart rate/training information is requested and obtained from the heart rate monitor and transferred to internal storage of the DLL by using the following function call:

```
// Read exercise files from HR monitor
if (!fnHRMCom_ReadExercisesData (hD1g, FALSE));        (15)
{
// Reading failed
}
```

Figure 8:
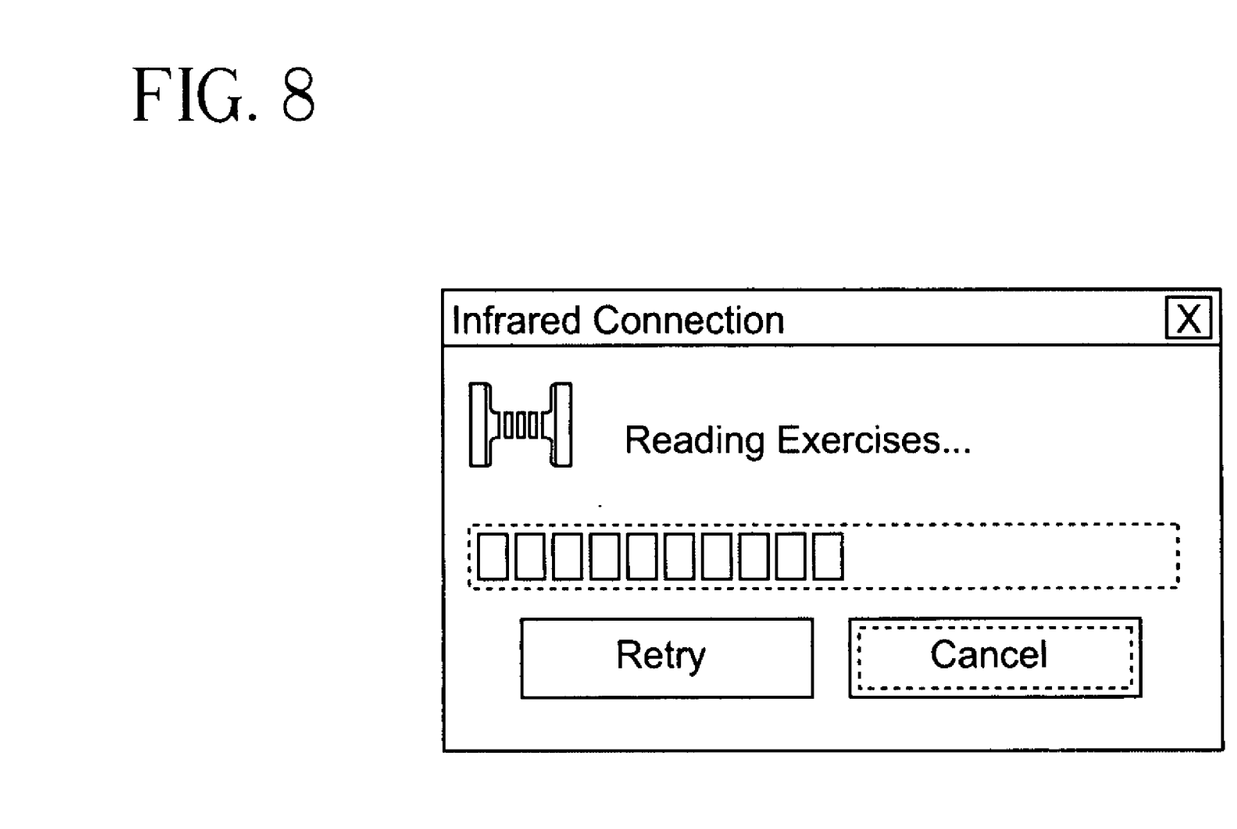
FIG. 8 is a pictorial representation of a dialog block indicating the progress of the transfer of file information from the heart rate monitor shown in FIG. 1.

By calling the function fnHRMCom_ReadExercisesData, a dialog box, such as that shown in FIG. 8, is preferably provided to indicate the progress of transferring the file information. When the function call directly above returns TRUE, all exercise files have preferably been transferred to internal storage of the DLL for further analysis.

Basic information concerning each exercise file read from the heart rate monitor is requested and obtained by using the following function call:

```
POLAR_EXERCISEFILE    PEF;                              (16)
ZeroMemory (&pef, sizeof(pet));                         (17)
if (!fnHRMCom_GetExeFileInfo (iExercise, &pef));        (18)
{
// Reading failed
}
```

In the function call above, the parameter iExercise represents the index of an exercise file, which preferably starts at zero. When the function call directly above returns TRUE, the structure pef preferably includes basic information about the selected (indexed) exercise file. A list of exercise files is preferably obtained from internal storage of the DLL by using the function fnHRMCom_GetExeFileInfo.

Since the internal storage area of the DLL preferably includes a maximum of 99 exercise files, an exercise file for further analysis must be specified. The function fnHRMCom_AnalyzeFile is called to specify the exercise file to be analyzed as follows:

```
// Analyze selected file information before reading it
if (!fnHRMCom_AnalyzeFile (iFileNbr, 0));               (19)
{
// Analyzing failed
}
```

The first parameter iFileNbr represents the zero-based index of the exercise file to be analyzed. The function fnHRMCom_ReadMonitorInfo is preferably used to obtain the total quantity of exercise files in the internal storage area of the DLL. The DLL preferably includes an automatic filtering capability for errors in the heart rate value, which can be activated by setting the second parameter to the following:
HRMCOM_PARAM_FILTERHRDATA.

When the function call directly above returns TRUE, all exercise information is ready in the internal storage area of the DLL.

To request and obtain general information concerning the exercise files, such as flags and parameters, the following function calls are preferably used:
bIntervals=fnHRMCom_GetRecFlags (FLAG_INTERVAL_DATA); and iSamplingRate=fnHRMCom_GetRecParam (REC_SAMPLING_RATE).

Additional flags are provided in the section entitled "HRM Data Flags" in the header file HRMCcom.h. Additional parameters are provided in the section entitled "HRM Data General Recording Information" in the header file HRMCom.h.

In step 88, prior to obtaining measured values or samples, the number of samples is preferably obtained by using the following function:
fnHRMCom_GetNbrOfHRMSamples.

Following this operation, samples are preferably obtained by calling the following function:
fnHRMCom_GetHRMSamples
in preferably the following way:

```
iTotal = fnHRMCom_GetNbrOfHRMSamples ( );               (20)
for (i = 0; i < iTotal; i++);                           (21)
{
iHR[i] = fnHRMCom_GetHRMSamples (CC_HRATE, i);
iSpeed[i] = fnHRMCom_GetHRMSamples (CC_SPEED, i);
}
```

The units of speed and altitude depend on a recording parameter REC_EURO_US_UNITS. To obtain the correct units, the following call is preferably used:

if (1==fnHRMCom_GetRecParam (REC_EURO_US_UNITS))        (22)

//Speed in mph, altitude in feet
else
//Speed in km/h, altitude in meters

Prior to obtaining lap time data, the quantity of laps is preferably obtained by using the following function call:
fnHRMCom_GetNbrOfIntTimes.

Following the function call directly above, lap information is preferably obtained by calling the following function:
fnHRMCom_GetIntTimeData
in preferably the following way:

```
iTotal = fnHRMCom_GetNbrOfIntTimes ( );                 (23)
for (i = 0; i < iTotal; i++)                            (24)
{
iTime = fnHRMCom_GetIntTimeData (i, INT_INT_TIME);      (25)
iHR = fnHRMCom_GetIntTimeData (i, INT_SAMPLE);          (26)
iSpeed = fnHRMCom_GetIntTimeData (i, INT_SPEED);        (27)
}
```

In step 90, if it is desired to return the heart rate monitor to a normal mode in response to termination of the transfer, such as watch mode in which the monitor displays the time-of-day, the following function call is preferably used:

POLAR_SSET_GENERAL psg;                                 (28)

//Fill general information

ZeroMemory (&psg, sizeof(psg));                         (29)

psg.iSize=sizeof (psg);                                 (30)

psg.iConnection=HRMCOM_CONNECTION_IR;                   (31)

psg.bConnectionDlg=TRUE;                                (32)

psg.hOwnerWnd=hDlg;                                     (33)

//Owner window handle

```
    fnHRMCom_SendMonitorToWatchMode (&psg);              (34)
```

However, the user may alternatively depress scroll buttons on the heart rate monitor to return to watch mode.

The following function call preferably terminates the connection thread of the DLL and closes the communication port:

fnHRMCom_EndIRCommunication (FALSE).

The following source code is a listing of a preferred implementation of C-code used to establish the infrared connection between the heart rate monitor and a pocket PC:

```
void fnPolarSampleConnection (HWND hWnd)                 (35)
{
    POLAR_SSET_GENERAL  psg;                             (36)
    POLAR_SSET_MONITORINFO  psmi;                        (37)
    POLAR_EXERCISEFILE  pef;                             (38)
    int  iSamplingRate, i, iTotal, iHR, iSpeed;          (39)
    if(!fnHRMCom_ResetIRCommunication (0))               (40)
    {
    // Resetting IR connection was not successful
    break;                                               (41)
    }
    if(!fnHRMCom_StartIRCommunication (0, "COM2:"))      (42)
    {
    // Port couldn't be opened, stop connection thread
    fnHRMCom_EndIRConmunication (FALSE);                 (43)
    break;                                               (44)
    }
    // Fill general information
    ZeroMemory (&psg, sizeof(psg));                      (45)
    psg.iSize = sizeof(psg);                             (46)
    psg.iConnection = HRMCOM_CONNECTION_IR;              (47)
    psg.bConnectionDlg = TRUE;                           (48)
    psg.hOwnerWnd = hWnd;                                (49)
    // Owner window handle
    // Reset monitor information
    ZeroMemory (&psmi, sizeof(psmi));                    (50)
    // Read monitor info from HR monitor using IR
    if(!fnHRMCom_ReadMonitorInfo (&psg, &psmi))          (51)
    {
    // Reading failed, close connection
    fnHRMCom_EndIRCommunication (FALSE);                 (52)
    break;                                               (53)
    }
    // Read exercise files from HR monitor
    if(!fnHRMCom_ReadExercisesData (hWnd, FALSE))        (54)
    {
    // Reading failed, close connection
    fnHRMCom_EndIRCommunication (FALSE);                 (55)
    break;                                               (56)
    }
    // Reset exercise information
    ZeroMemory (&pef, sizeof(pef));                      (57)
    // Get first exercise's info
    if(!fnHRMCom_GetExeFileInfo (0, &pef))               (58)
    {
    // Reading failed, close connection
    fnHRMCom_EndIRCommunication (FALSE);                 (59)
    break;                                               (60)
    }
    // Analyze selected file information before reading it
    if(!fnHRMCom_AnalyzeFile (0, 0))                     (61)
    {
    // Analyzing failed, close connection
    fnHRMCom_EndIRCommunication (FALSE);                 (62)
    break;                                               (63)
    }
    // Read sampling (recording) rate
    iSamplingRate = fnHRMCom_GetRecParam                 (64)
    (REC_SAMPLING_RATE);
    // Read total number of samples
    iTotal = fnHRMCom_GetNbrOfHRMSamples ( );            (65)
    // Get all heart rate and speed values
    for (i = 0; i < iTotal; i++)                         (66)
    {
    iHR = fnHRMCom_GetHRMSamples (CC_HRATE, i);          (67)
    iSpeed = fnHRMCom_GetHRMSamples (CC_SPEED, i);       (68)
    }
    if(1 == fnHRMCom_GetRecParam                         (69)
    (REC_EURO_US_UNITS))
    {
    // Speed in mph, altitude in feet
    }
    else                                                 (70)
    {
    // Speed in km/h, altitude in meters
    }
    // Set HR monitor to watch mode
    fnHRMCom_SendMonitorToWatchMode (&psg);              (71)
    // End IR communication
    fnHRMCom_EndIRCommunication (FALSE);                 (72)
}
```

Figure 9:
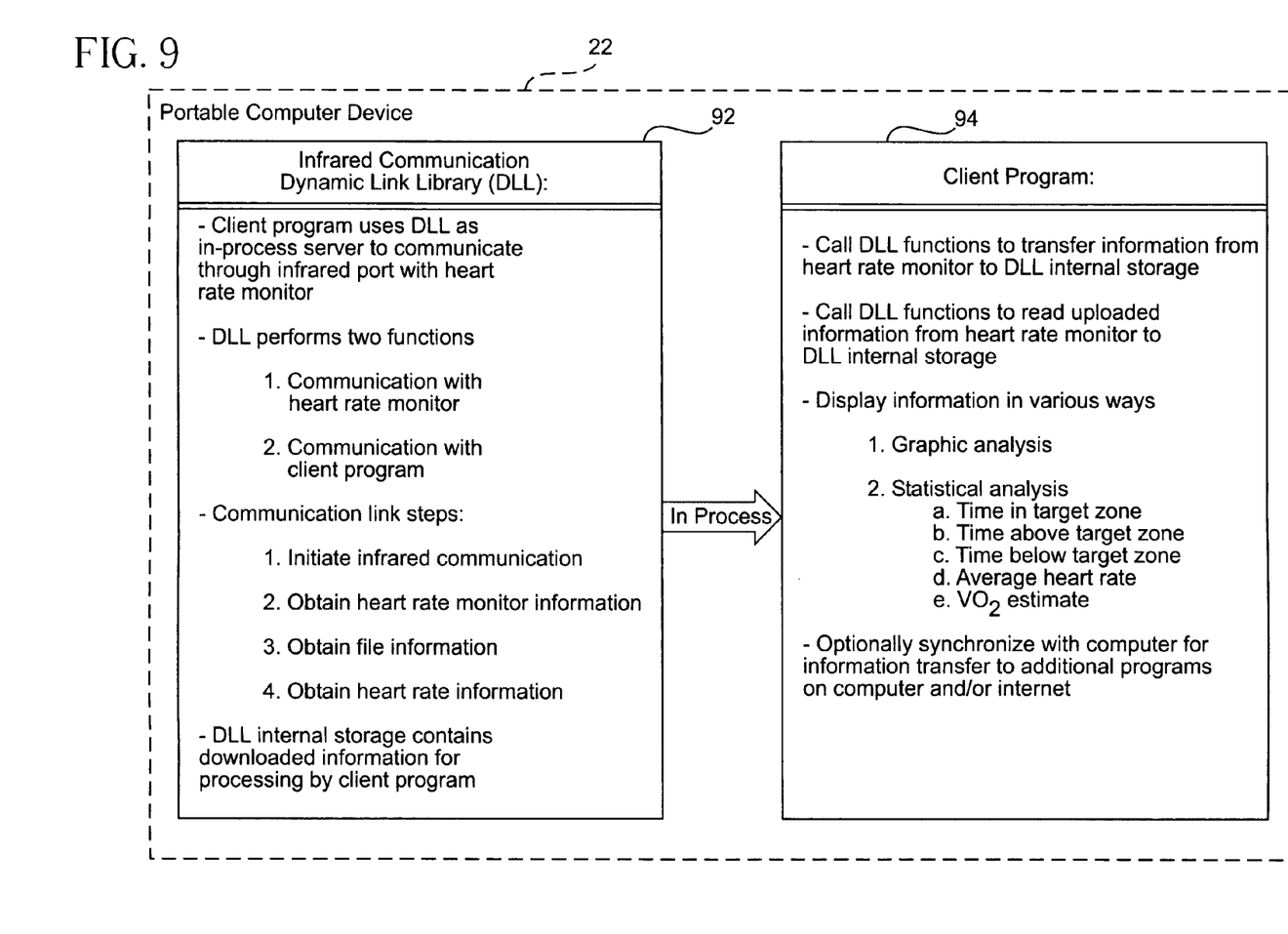
FIG. 9 is a block diagram showing the interaction of software systems within the portable computer device shown in FIG. 1; and A header file HRMCom.h for the DLL software platform HRMCom.DLL is incorporated as a portion of this document as an appendix.

FIG. 9 shows a block diagram of the two primary software programs resident in the PCD that are responsible for the infrared communication link and additional processing and analysis of the transferred information. The maximum infrared transfer distance is preferably about 20 centimeters or 8 inches, and the infrared transfer angle is preferably about ±15°. An IR communication dynamic link library (DLL) 92 is used by a client program 94 as an in-processor server to communicate through the infrared port with the heart rate monitor.

The DLL 92 communicates with the heart rate monitor and the client program 94. Client usage preferably includes initiation of the infrared communication; requesting and obtaining monitor information; requesting and obtaining file information; and requesting and obtaining specific heart rate information. An internal storage area in the DLL 92 contains the uploaded information for processing by the client program 94.

The client program 94 calls functions in the DLL 92 to transfer information from the heart rate monitor to the DLL 92 internal storage and read uploaded information from the DLL 92 internal storage. The client program 94 also displays and performs analysis of the information, such as graphical and statistical analysis (time in the target heart rate zone, time above the target heart rate zone, time below the target heart rate zone, average heart rate, and $VO_2$ estimate). The client program 94 optionally synchronizes with the PCD for information transfers to additional programs in the PCD and/or Internet.

Therefore, the method and apparatus formed in accordance with the present invention processes heart rate information by bidirectionally exchanging setting information, which may be used to program a heart rate monitor, and exchanging measured data, such as heart rate and training information, between a heart rate monitor and a PCD. Further, the method and apparatus substantially simplify the process of programming the heart rate monitor and reduce the amount of time required by the user to initialize the monitor prior to its use. In addition, the method and apparatus of the subject invention enable measured heart rate and training information to be downloaded, processed, and analyzed by the PCD.

Although the illustrative embodiments of the present invention have been described herein with reference to the accompanying drawings, it is to be understood that the invention is not limited to those precise embodiments and that various other changes and modifications may be effected therein by one skilled in the art without departing from the scope or spirit of the invention.

What is claimed is:

1. A method of processing heart rate information in a portable computer device comprising monitoring by a wearable heart rate monitor and wirelessly transferring the heart rate information between the wearable heart rate monitor and the portable computer device, the method comprising the steps of:
   initiating a connect mode in the wearable heart rate monitor, the connect mode enabling a wireless communication link to be established with the wearable heart rate monitor;
   initiating transfer software in the portable computer device, the transfer software controlling the transfer of information between the wearable heart rate monitor and the portable computer device through the wireless communication link, the information including setting information adapted to program the wearable heart rate monitor;
   transferring the setting information bidirectionally between the wearable heart rate monitor and the portable computer device through the communication link comprising:
      initiating a batch heart rate/training information transfer mode in the portable computer device;
      transferring batch heart rate/training information from the heart rate monitor to the portable computer device comprising initiating wireless communication with the heart rate monitor by the portable computer device; requesting heart rate monitor information from the heart rate monitor by the portable computer device; transferring the heart rate monitor information from the heart rate monitor to the portable computer device; requesting file information from the heart rate monitor by the portable computer device; transferring the file information from the heart rate monitor to the portable computer device; requesting heart rate information from the heart rate monitor by the portable computer device comprising requesting a quantity of samples, information associated with at least one of the samples, a quantity of laps, and information associated with at least one of the laps; transferring the heart rate information from the heart rate monitor to the portable computer device; storing the heart rate information in the portable computer device;
      returning the heart rate monitor to a normal mode in response to completion of the batch transfer of the heart rate/training information; and
   processing the heart rate information in the portable computer device.

2. A method of processing heart rate information in a portable computer device comprising monitoring by a heart rate monitor and wirelessly transferring the heart rate information between the heart rate monitor and the portable computer device as defined by claim 1, wherein the step of processing further includes the step of displaying the processed information on the portable computer device.

3. A method of processing heart rate information in a portable computer device comprising monitoring by a heart rate monitor and wirelessly transferring the heart rate information between the heart rate monitor and the portable computer device as defined by claim 1, wherein the wireless communication link is Bluetooth.

4. A method of processing heart rate information in a portable computer device comprising monitoring by a heart rate monitor and wirelessly transferring the heart rate information between the heart rate monitor and the portable computer device as defined by claim 1, further comprising the step of connecting a first wireless communication interface to the portable computer device and a second wireless communication interface to the heart rate monitor, the first wireless communication interface enabling the portable computer device to communicate through the communication link, the second wireless communication interface enabling the heart rate monitor to communicate through the communication link.

5. A method of processing heart rate information in a portable computer device comprising monitoring by a heart rate monitor and wirelessly transferring the heart rate information between the heart rate monitor and the portable computer device as defined by claim 1, further comprising the step of maintaining at least one of a physical location between and an orientation of at least one of the heart rate monitor and the portable computer device during the transfer of the information.

6. A method of processing heart rate information in a portable computer device comprising monitoring by a heart rate monitor and wirelessly transferring the heart rate information between the heart rate monitor and the portable computer device as defined by claim 1, wherein the portable computer device includes at least one of a personal digital assistant (PDA), pocket personal computer (pocket PC), and laptop computer.

7. A method of processing heart rate information in a portable computer device comprising monitoring by a heart rate monitor and wirelessly transferring the heart rate information between the heart rate monitor and the portable computer device as defined by claim 1, wherein the information includes at least one of setting information, heart rate information, and training information.

8. A method of processing heart rate information in a portable computer device comprising monitoring by a heart rate monitor and wirelessly transferring the heart rate information between the heart rate monitor and the portable computer device as defined by claim 1, wherein the step of transferring the information between the heart rate monitor and the portable computer device includes at least one of the steps of uploading the information from the portable computer device to the heart rate monitor and downloading the information from the heart rate monitor to the portable computer device.

9. A method of processing heart rate information in a portable computer device comprising monitoring by a heart rate monitor and wirelessly transferring the heart rate information between the heart rate monitor and the portable computer device as defined by claim 1, wherein the step of initiating transfer software in the portable computer device includes the step of initiating transfer setting information software in the portable computer device, the transfer setting information controlling the transfer of setting information between the heart rate monitor and the portable computer device.

10. A method of processing heart rate information in a portable computer device comprising monitoring by a heart rate monitor and wirelessly transferring the heart rate information between the heart rate monitor and the portable computer device as defined by claim 1, wherein the step of initiating transfer software in the portable computer device includes the step of initiating transfer heart rate/training information software in the portable computer device, the heart rate/training information software controlling the transfer of heart rate/training information from the heart rate monitor to the portable computer device.

11. A method of processing heart rate information in a portable computer device comprising monitoring by a heart rate monitor and wirelessly transferring the heart rate information between the heart rate monitor and the portable computer device as defined by claim 1, wherein the step of transferring the information between the heart rate monitor and the portable computer device includes the steps of:
   initiating an upload setting information mode in the portable computer device;
   uploading setting information from the portable computer device to the heart rate monitor; and
   returning the heart rate monitor to a normal mode in response to completion of the upload of the setting information.

12. A method of processing heart rate information in a portable computer device comprising monitoring by a heart rate monitor and wirelessly transferring the heart rate information between the heart rate monitor and the portable computer device as defined by claim 1, wherein the step of transferring the information between the heart rate monitor and the portable computer device includes the steps of:
   initiating a download setting information mode in the portable computer device;
   downloading setting information from the heart rate monitor to the portable computer device; and
   initiating a normal mode in the heart rate monitor in response to completion of the download of the setting information.

13. A method of processing heart rate information in a portable computer device comprising monitoring by a heart rate monitor and wirelessly transferring the heart rate information between the heart rate monitor and the portable computer device as defined by claim 1, wherein the step of initiating wireless communication with the heart rate monitor by the portable computer device includes the step of initializing a serial port on the portable computer device.

14. A method of processing heart rate information in a port able computer device comprising monitoring by a heart rate monitor and wirelessly transferring the heart rate information between the heart rate monitor and the portable computer device as defined by claim 1, wherein the step of requesting file information from the heart rate monitor by the portable computer device includes at least one of the steps of verifying whether the heart rate information has been substantially completely transferred to the portable computer device in the form of files, specifying the index of at least one of the transferred files to be processed by the portable computer device, and requesting information associated with at least one of the transferred files.

15. A method of processing heart rate information in a portable computer device comprising monitoring by a heart rate monitor and wirelessly transferring the heart rate information between the heart rate monitor and the portable computer device as defined by claim 1, wherein the step of transferring the file information from the heart rate monitor to the portable computer device includes the step of transferring information associated with at least one of the transferred files.

16. A method of processing heart rate information in a portable computer device comprising monitoring by a heart rate monitor and wirelessly transferring the heart rate information between the heart rate monitor and the portable computer device as defined by claim 1, wherein the step of transferring the heart rate information from the heart rate monitor to the portable computer device includes the step of transferring a quantity of samples, information associated with at least one of the samples, a quantity of laps, and information associated with at least one of the laps.

17. A method of processing heart rate information in a portable computer device comprising monitoring by a heart rate monitor and wirelessly transferring the heart rate information between the heart rate monitor and the portable computer device as defined by claim 1, further comprising the step of terminating wireless communication with the heart rate monitor by the portable computer device.

18. A method of processing heart rate information in a portable computer device comprising monitoring by a heart rate monitor and wirelessly transferring the heart rate information between the heart rate monitor and the portable computer device as defined by claim 1, further comprising the step of processing the heart rate information by the portable computer device.

19. A method of processing heart rate information in a portable computer device comprising monitoring by a heart rate monitor and wirelessly transferring the heart rate information between the heart rate monitor and the portable computer device as defined by claim 18, wherein the step of processing the heart rate information in the portable computer device further includes the step of performing at least one of graphical analysis and statistical analysis.

20. A method of processing heart rate information in a portable computer device comprising monitoring by a heart rate monitor and wirelessly transferring the heart rate information between the heart rate monitor and the portable computer device as defined by claim 18, wherein the step of processing the heart rate information by the portable computer device includes the step of calculating at least one of a duration of time in a target heart rate zone, a duration of time above the target heart rate zone, a duration of time below the target heart rate zone, an average heart rate, and a $VO_2$ level.

21. A method of processing heart rate information in a portable computer device comprising monitoring by a heart rate monitor and wirelessly transferring the heart rate information between the heart rate monitor and the portable computer device as defined by claim 1, further comprising the step of synchronizing the transfer of heart rate information with a program on at least one of the portable computer device and the Internet.

22. A method of processing heart rate information in a portable computer device comprising monitoring by a heart rate monitor and wirelessly transferring the heart rate information between the heart rate monitor and the portable computer device as defined by claim 1, wherein the step of transferring the information between the heart rate monitor and the portable computer device includes the steps of:
   initiating a real-time heart rate/training information transfer mode in the portable computer device;
   transferring heart rate/training information from the heart rate monitor to the portable computer device in substantially real-time; and
   returning the heart rate monitor to a normal mode in response to completion of the substantially real-time transfer of the heart rate/training.

* * * * *